United States Patent [19]

Arison et al.

[11] Patent Number: 5,192,671
[45] Date of Patent: Mar. 9, 1993

[54] PROCESS FOR THE GLYCOSYLATION OF AVERMECTIN COMPOUNDS

[75] Inventors: Byron H. Arison, Watchung; Marvin D. Schulman, Scotch Plains; Patrick J. Doherty, Edison, all of N.J.

[73] Assignee: Merck & Co., Inc., Rahway, N.J.

[21] Appl. No.: 721,744

[22] Filed: Jun. 26, 1991

[51] Int. Cl.$^5$ .............................................. C12P 19/04
[52] U.S. Cl. ..................................... 435/101; 435/46; 435/100; 536/7.1
[58] Field of Search ............................ 536/7.1; 435/76

[56] References Cited

U.S. PATENT DOCUMENTS

| | | | |
|---|---|---|---|
| 2,653,899 | 4/1952 | Bunch et al. | 435/76 |
| 2,834,714 | 3/1954 | Denison et al. | 435/7.1 |
| 3,801,465 | 4/1974 | Martin et al. | 536/7.1 |
| 4,203,976 | 5/1980 | Fisher et al. | 424/180 |
| 4,310,519 | 1/1982 | Albers-Schonberg et al. | 424/181 |
| 4,469,682 | 9/1984 | Mrozik | 536/7.1 |

FOREIGN PATENT DOCUMENTS 317148 11/1987 European Pat. Off. .
0463677 6/1991 European Pat. Off. .

OTHER PUBLICATIONS

Corcoran, (1981) *Antibiotics, vol. 4, pp. 132–174.*
Metzler, (1977) *Biochemistry,* Chapter 10, pp. 615–623.
Mathews et al. (1990) *Biochemistry,* Chapter 15, pp. 532–533.
Styren (1975) *Biochemistry,* 3rd Ed., pp. 339–341.
Goldstein et al. (1978) *Antibiotics,* vol. 31(1), pp. 63–69.
Metzler (1977) *Biochemistry,* Chapter 11 and 12, pp. 659–698.
Corcoran et al Methods in Enzymology 43. pp. 487–498 (1975).
Int. J. Syst. Bacteriol. 37 pp. 19–22 (1987).
Int. J. Syst. Bacteriol. 30 p. 380 (1980).
Arch. Microbiol. 31 p. 353 (1958).
Wang et al. *Biological Abstracts,* vol. 83(2), Jan. 15, 1987, #10142.
Springer et al., *J. Am. Chem. Soc., vol. 103(14), Jul. 15, 1981, pp. 4221–4224.*
Schulman et al., J. Antibiotics, vol. 39(4), Apr. 1986, pp. 541–549.

*Primary Examiner*—Johnnie R. Brown
*Assistant Examiner*—Pamela S. Webber
*Attorney, Agent, or Firm*—David L. Rose; Joseph F. DiPrima

[57] ABSTRACT

Avermectin compounds are glycosylated the 4' and 4"-positions by adding the avermectin compounds to the fermentation medium of *Saccharapolyspora erythrea*. The outer oleandrose sugar group of the avermectin compound is glycosylated with a glycosyl moiety, specifically a glucose group. In addition, other changes are effected in the avermectin moiety such as selective hydroxylation, epimerization at the 2-carbon and migration of the Δ 3-double bond to a Δ 2-position.

5 Claims, No Drawings

PROCESS FOR THE GLYCOSYLATION OF AVERMECTIN COMPOUNDS

BACKGROUND OF THE INVENTION

Avermectin compounds are natural products produced by the fermentation of *Streptomyces avermitilis* as disclosed in U.S. Pat. No. 4,310,519 to Albers-Schonberg et al. The avermectin compounds have a natural α-L-oleandrosyl-α-L-oleandrosyloxy group at the 13-position. In U.S. Pat. No. 4,203,976 to Fischer et al certain synthetic procedures are disclosed for glycosylting various hydroxy groups or the avermectin molecule, including the 4"-hydroxy of the avermectin disaccharide group. The culture *Saccharopolyspora erythrea* identified in the culture collection of Merck & Co., Inc. as MA 1625 is a known culture, publicly available from the American Type Culture Collection at 12301 Parklawn Drive, Rockville, MD 20852, under the accession number ATCC 11635, and further described in Corcoran, *Methods in Enzymology* 43 pg 487–498 (1975).

SUMMARY OF THE INVENTION

This invention is concerned with the preparation of avermectin compounds with a glucose group substituted at the 4"-position of the natural, 13-(α-L-oleandrosyl-α-L-oleandrosyloxy) group or at the 4'-position of the 13. (α-L-oleandrosyl) group of the avermectin monosaccharide which are prepared by fermenting an avermectin compound in a culture medium of *Saccharopolyspora erythrea* MA 1625, ATCC 11635. Thus, it is an object of this invention to describe the avermectin compounds prepared in such fermentation medium. It is a further object of this invention to describe the processes used the prepare such compounds. It is a still further object to describe the antiparasitic uses of such compounds. Another object of this invention is to describe the additional modification of the avermectin compounds which are observed following such fermentation. Additional objects will become apparent from a reading of the following description.

DESCRIPTION OF THE INVENTION

This invention is concerned with the preparation of avermectin trisaccharide and disaccharide compounds where a glucose group is placed at the 4' and 4"-positions of an avermectin compound. The process is carried out by culturing the microorganism *Saccharopolyspora erythrea* in a culture medium and adding the avermectin starting material to the fermentation broth. The culture *S. erythrea* is a well-known microorganism that is readily available from the American Type Culture Collection under the accession number ATCC 11635. The morphological and cultural characteristics of *S. erythrea* are described in *Int. J. Syst. Bacteriol*, 37 pg 19–22 (1987), *Int. J. Syst. Bacteriol*, 30 pg 380 (1980) and *Arch. Microbiol*, 31 pg 353 (1958).

The process of the instant invention is best realized in the following reaction scheme:

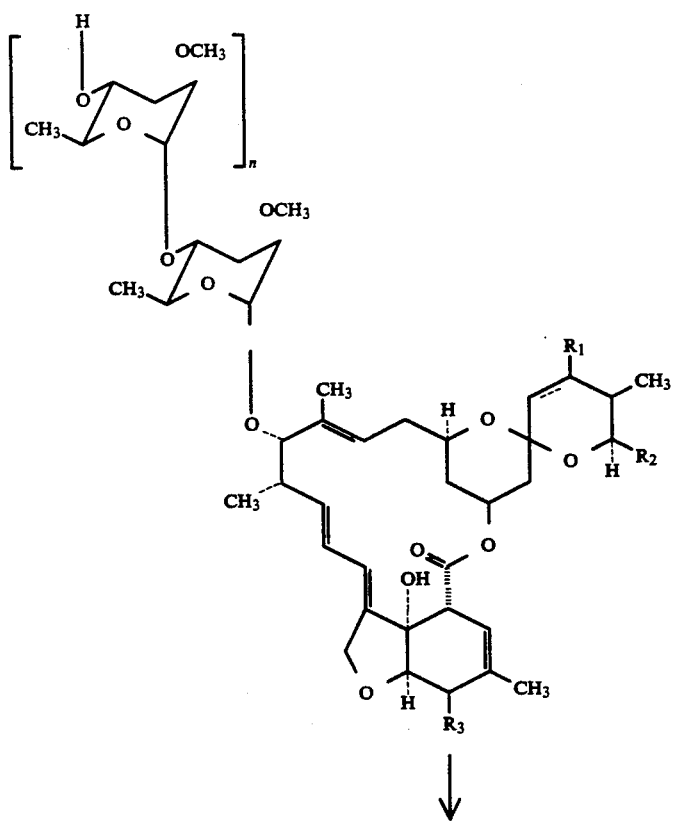

I

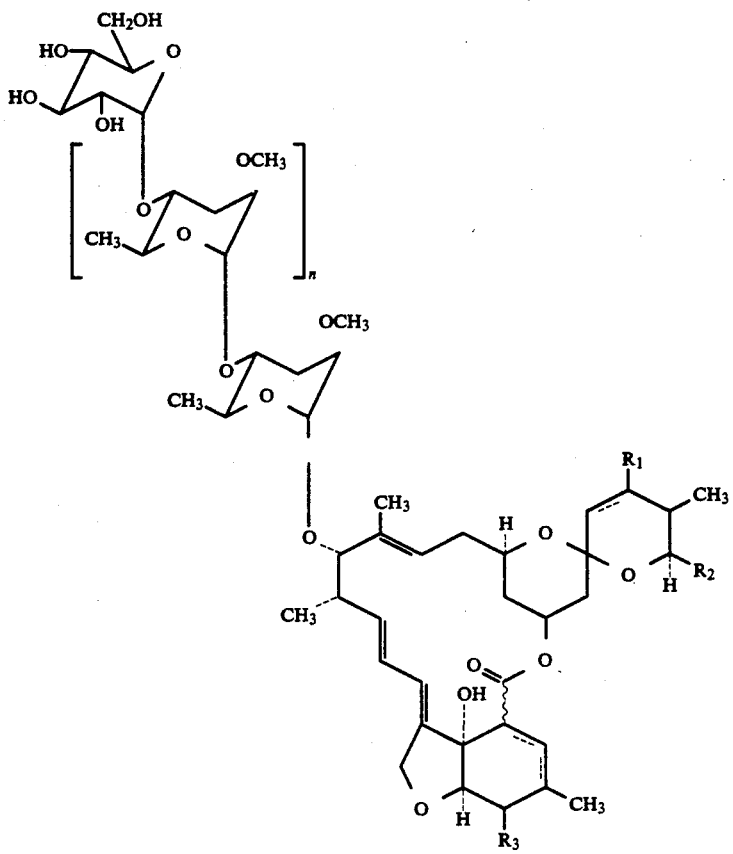

In the above reaction scheme the broken line at the 22,23-position indicates a single or a double bond at the 22,23-position;

n is 0 or 1;

$R_1$ is present only when the broken line represents a single bond at the 22,23-position and is hydrogen or hydroxy;

$R_2$ is alkyl of 1 to 8 carbon atoms, alkenyl of 2 to 8 carbon atoms or cycloalkyl at 3 to 8 carbon atoms;

$R_3$ is hydroxy or methoxy; and the broken line at the 2,3,4-positions indicate a double bond at either the 2,3-position or at the 3,4-position.

The above compounds of Formula II are novel compounds and are active anthelmentic agents. They are to be considered as part of the instant invention.

The instant process is carried out by adding a compound of Formula I to the fermentation broth of S. erythrea and carrying out the fermentation as described below. The compound of Formula I can be added to the fermentation broth at any time during the fermentation period however it has been found advantageous to add the starting material after allowing the fermentation to proceed for a portion of its term but, to allow the microorganism sufficient time to operate on the starting material, before the fermentation term is complete. Generally, the starting material is added after the fermentation term is at least 10% complete but before it is 75% complete. Preferably the starting material is added when the fermentation has completed from 20% to 50% of its scheduled term.

The starting material is added to the fermentation broth in quantities of from 0.1 to 10 mg per liter of fermentation broth. Preferably the starting material is added in quantities of from 1 to 8 mg per ml. of fermentation broth.

The preferred compounds of the instant invention are realized when in the above structural Formula II:

the broken line at the 22,23-position indicates a 22,23-single bond and $R_1$ is hydrogen;

$R_2$ is isopropyl or sec-butyl;

$R_3$ is hydroxy; and the broken line at the 2,3,4-position indicates a 3,4-double bond.

The above described strain of *Streptomyces erythrea* MA-1625, ATCC 11635 is illustrative of a strain which can be employed in the production of the instant compounds. However, the present invention also embraces mutants of the above described microorganism. For example, those mutants which are obtained by natural selection of those produced by mutating agents including ionizing radiation such as ultraviolet irradiation, or chemical mutagens such as nitrosoguanidine or the like treatments are also included within the ambit of this invention.

The instant compounds are produced during the aerobic fermentation of suitable aqueous nutrient media under conditions described hereinafter, with a producing strain of *Streptomyces erythrea* MA-1625, ATCC 11635. Aqueous media such as those used for the production of many antibiotic substances are suitable for use in this process for the production of this macrocyclic compound. Such nutrient media contain sources of carbon and nitrogen assimilable by the microorganism and generally low levels of inorganic salts. In addition, the fermentation media may contain small amounts of inorganic salts and traces of metals necessary for the growth of the microorganisms, and production of the desired compounds. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 0.5 and 5% by weight of the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Saccharppolyspora erythrea* MA-1625, ATCC 11635 in the production of the instant compounds. The various sources of nitrogen can be used alone or in combination in amounts ranging from 0.2 to 6% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of *Saccharopolyspora erythrea* MA-1625, ATCC 11635.

| MEDIUM 1 | |
|---|---|
| Glucose | 5 g |
| Commerical Brown Sugar | 10 g |
| Tryptone | 5 g |
| Yeast Extract | 2.5 g |
| EDTA (ethylene diamine tetracetic acid) | 36 mg |
| betaine | 1.29 g |
| sodium propionate | 0.11 g |
| distilled H$_2$O | 1100 ml |
| pH 7.0–pH 7.2 | |
| MEDIUM 2 | |
| Sucrose | 15 g |
| Peptone | 5.0 g |
| Yeast extract | 2.5 g |
| L-arginine | 0.5 g |
| Distilled H$_2$O | 1000 ml |
| pH 7.0 | |
| MEDIUM 3 | |
| Glucose | 50 g |
| NaCl | 5.0 g |
| (NH$_4$)$_2$SO$_4$ | 2.0 g |
| CaCO$_3$ | 6.0 g |
| propanol | 5 g |
| soya flour | 30 g |
| distilled H$_2$O | 1000 ml |
| MEDIUM 4 | |
| Soluble starch | 15 g |
| Soytone | 20 g |
| CaCl$_2$ | 0.1 g |

| -continued | |
|---|---|
| yeast extract | 1.5 g |
| soya oil | 50 ml |
| MOPS (Morpholino propane sulfonic acid) | 10 5 ml |
| MEDIUM 5 | |
| K$_2$HPO$_4$ | 450 mg |
| saccharose | 2.0 g |
| casein | 1.5 g |
| NaCl | 50 mg |
| L-arginine | 15 mg |
| trace element mix A | 1.0 ml |
| distilled water | 1000 ml |
| pH 6.9 | |
| TRACE ELEMENT MIX | |
| Citric Acid | 46.2 mg |
| FeSO$_4$.7H$_2$O | 2.0 mg |
| ZnSO$_4$.7H$_2$O | 1.0 mg |
| MnCl$_2$.4H$_2$O | 0.8 mg |
| CoCl$_2$.6H$_2$O | 0.1 mg |
| MgSO$_4$.7H$_2$O | 50 ml |
| Ascobic acid | 0.12 mg |
| H$_2$O | 160 ml |
| MEDIUM 6 | |
| Cottonseed oil | 5.0 g |
| yeast extract | 0.5 g |
| dextrose | 4.5 g |
| soybean oil | 0.5 ul |
| CaCO3 | 0.6 g |
| Trace element mix | 1.0 ml |
| distilled H$_2$O | 1000 ml |

The fermentations employing *Saccharopolyspora erythrea* MA-1625, ATCC 11635 can be conducted at temperatures ranging from about 20° C. to about 40° C. For optimum results, it is most convenient to conduct these fermentations at a temperature in the range of from about 24° C. to about 30° C. Temperatures of about 27°–28° C. are most preferred. The pH of the nutrient medium suitable for producing the instant compounds can vary from about 5.0 to 8.5 with a preferred range of from about 6.0 to 7.5.

Small scale fermentations are conveniently carried out by placing suitable quantities of nutrient medium in a flask employing known sterile techniques, inoculating the flask with either spores or vegetative cellular growth of *Saccharopolyspora erythrea* MA-1625, ATCC 11635, loosely stoppering the flask with cotton and permitting the fermentation to proceed in a constant room temperature of about 30° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Saccharopolyspora erythrea* MA-1625, ATCC 11635. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 500 RPM and about 50 to 500 liters per minute of air.

The novel compounds of this invention are found primarily in the aqueous portion of the fermentation medium on termination of the *Streptomyces erythrea* MA-1625, ATCC 11635 fermentation and may be removed and separated therefrom as described below.

The separation of the novel compounds from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentaion broth is combined with approximately an equal volume of an organic solvent. While any organic solvent may be employed, it is preferable to use a water immiscible solvent such as ethyl acetate, methylene chloride, chloroform, methyl ethyl ketone and the like. Generally several extractions are desirable to achieve maximum recovery. The solvent removes the instant compounds as well as other substances lacking the antiparasitic activity of the instant compounds. If the solvent is a water immiscible one, the layers are separated and the organic solvent is evaporated under reduced pressure. If the solvent is water miscible, it can be extracted with a water immiscible solvent to separate the entrained water. This solvent can then be concentrated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride, chloroform or hexane to further remove impurities, and is then washed with a mixture of methylene chloride, chloroform or hexane and an organic solvent of which acetone, ethyl acetate, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, dextran gels and the like, as the chromatographic medium, with various solvents and combinations of solvents as the eluent. Thin layer, high pressure, liquid and preparative layer chromatography may be employed to detect the presence of, and to isolate the instant compounds. The use of the foregoing techniques as well as other known to those skilled in the art, will afford purified compositions containing the instant compounds. The presence of the desired compounds is determined by analyzing the various chromatographic fractions for biological activity against selected parasites, or physicochemical characteristics. The structures of the instant compounds has been determined by detailed analysis of the various spectral characteristics of the compounds, in particular their nuclear magnetic resonance, mass, ultraviolet and infrared spectra.

The instant compounds are potent endo-and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating diperous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also actove against household pests such as the cockroach, Blatella sp., clothes moth, Tineola sp., carpet beetle, Attagenus sp., the housefly *Musca domestica* as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are broght back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally indlucing one or more additiona active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area applications, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administratered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

1-4"-O-Glucosyl ivermectin

*S. erythraea* (ATCC 11635) was grown in medium M102 as described by Corcoran (*Methods in Enzymology* 43: 487–498 1975). It contained the following in 1000 ml of distilled water: glucose, 5 g; commercial brown sugar (Domino's), 10 g; tryptone, 5 g; yeast extract, 2.5 g; ethylene diamine tetraacetate, 0.036 g; betaine, 1.2 g; sodium propionate, 0.11 g. The medium was adjusted to pH 7.0–7.2 and 2 ml of trace elements solution which contained the following in g/l were added $FeCl_3.6H_2O$, 0.2; $ZnCl_2$, 0.04; $MnCl_2.4H_2O$; 0.01; $CuCl_2.2H_2O$, 0.01; $NaB_4O_7.10H_2O$, 0.01; $(NH_4)_6Mo_7O_{24}.4H_2O$, 0.01.

INOCULUM PREPARATION

Frozen vegetative mycelia (FVM) were prepared by inoculating 250 ml medium 102 in a 2 liter 3 baffle flask and incubating at 32° C., 85% relative humidity and 200 RPM for 48 hours. The packed cell volume of the culture was 10% and the pH 6.9. Aliquots of the culture was frozen and used as source of inoculum for future experiments.

SEED CULTURE

To 40 ml of medium M102 in a 250 ml flask, 1.0 ml of FVM was added as inoculum and the flasks were incubated at 30° C., 85% relative humidity and 200 RPM for 40 hours.

BIOTRANSFORMATION AND ISOLATION

To 40 ml of medium M102 in a 250 ml flask, 1.0 ml of seed culture was added and the flasks were incubated at 30° C., 85% relative humidity at 200 RPM for 24 hours. 2.5 g of ivermectin (22,23 dihydro avermectin Bla/Blb) in 0.1 ml DMSO were added and the flasks were incubated as above for 5 days. Each flasks was extracted with $2 \times 80$ ml portions of $CH_2Cl_2$. The $CH_2Cl_2$ extracts were combined, concentrated and the avermectins were partially purified by preparative TLC on silica gel 50 using methylene chloride: ethylacetate: methanol (9.9:1) as the solvent. The individual avermectin bands were eluted from the silica, concentrated and further purified by HPLC on Dupont Zorbax ODS using $CH_3OH:H_2O$ 90:10, 85:15 80:20 or 70:30) as the mobile phase. The structures of the purified avermectins were determined by mass spectroscopy and NMR spectroscopy The HPLC retention times of 4"-O-glucosyl ivermectin on a Dupont Zorbax ODS column with $CH_3OH:H_2O$ at 1 ml/min as the mobile phase is 7.2 min at 90:10, 18.7 min at 85:15 at 40.9 min at 80:20. The molecular weight determined by mass spectroscopy is 1036. Characteristic NMR spectroscopy signals of this derivative are: 4.45d, J=7, H-1 (glucose), ca 3.37 m. H-2 (glucose). This compound is nearly as potent an anthelmintic as invermectin, but is greater than 10-fold safer.

EXAMPLE 2

4"-O-Glucosyl avermectin Bla

Procedure was the same as example 1 except 2.5 mg of avermectin Bla in 0.1 ml DMSO were added to the biotransformation flasks. The HPLC retention times on a Dupont Zorbax ODS column with $CH_3OH:H_2O$ at 1 mg/min as the mobile phase are 5.5 min at 90:10, 10.2 min at 85:15 and 20:3 min at 80:20. The molecular weight determined by mass spectroscopy is 1034. Characteristic NMR spectroscopy signal are: 4.45H,8 H1 (glucose), 3.38 m. H-2 (glucose).

This derivative is nearly as potent an anhelmintic and insecticide as avermectin Bla but is greater than 10 fold safer.

EXAMPLE 3

4"-O-Glucosyl 22,23 dihydro avermectin Blb

Procedure was the same as example 1 except 0.5 mg of 22,23 dihydro avermectin Blb was added to the biotransformation flasks. The HPLC retention times on a Dupont Zorbax ODS column with $CH_3OH:H_2O$ at 1 ml/min as the mobile phase are 6.4 min at 90:10, 15.2 min at 85:15 at 32.5 min at 80:20. The molecular weight determined by mass spectroscopy of 1024.

EXAMPLE 4

4"-O-Glucosyl avermectin Blb

Procedure was the same as example 1 except 0.5 mg of avermectin Blb was added to the biotransformation flasks. The HPLC retention times on a Dupont Zorbax ODS column with $CH_3OH:H_2O$ at 1 mg/min as the mobile phase are 5.0 min at 90:10, 8.75 min at 85:15, 15.87 min at 80:20. The molecular weight determined by mass spectroscopy of 1022. Characteristic NMR signals are: 4.43d, 7.5. H 1. glucose; methyl doublets at 0.92 (6H). 1.09, 1.74, 1.22 and 1.31 (last two represent olendrose methyls).

EXAMPLE 5

4'-O-Glucosyl 22,23 dihydro avermectin Bla/Blb monosaccharide

Procedure was the same as example 1 except 2.5 mg of 22,23-dihydro avermectin Bla/Blb monosaccharide were added to the biotransformation flasks. The HPLC retention times of this derivative on a Dupont Zorbax ODS column with $CH_3OH:H_2O$ at 1 ml/min the mobile phase are 11.3 min at 85:15, and 20.7 min at 80:20. The molecular weight determined by mass spectroscopy of 892. Characteristic NMR spectroscopy peaks are: 4.62d. J=8, H-1(glucose), (glucose). 3.18dd. J=10,8. H-2 (glucose).

EXAMPLE 6

4'-O-Glucosyl avermectin Bla monosaccharide

Procedure was the same as example 1 except 2.5 mg of avermectin Bla monosaccharide was added to the biotransformation flasks. The HPLC retention times of this derivative on a Dupont Zorbax ODS column with $CH_3OH:H_2O$ as mobile phase are 6.61 min at 85:15, at 80:20. The molecular weight determined by mass spectroscopy of 890. Characteristic NMR spectroscopy peaks are: 4.62d. J=8, H-1 (glucose), 3.18dd, 10.8. H-2 (glucose).

What is claimed is:

1. A process for the preparation of a compound having the formula:

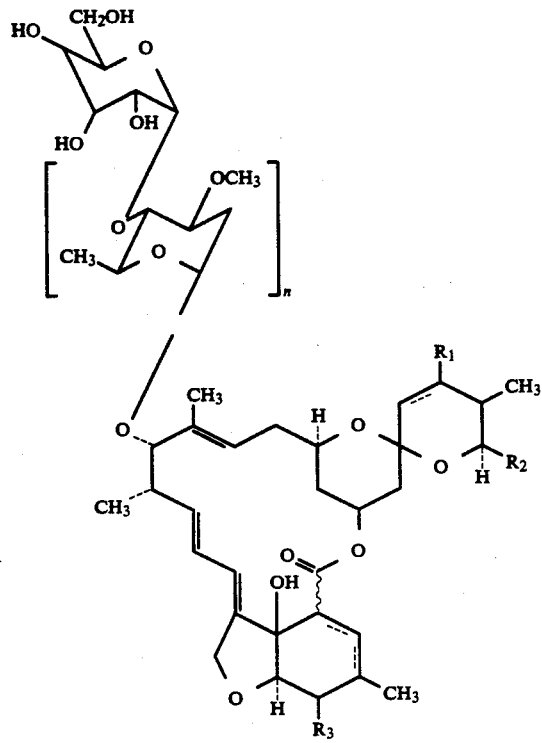

wherein the broken line at the 22, 23-position indicates a single or a double bond at the 22, 23-position;
n is 1 or 2
R$_1$ is present only when the broken line represents a single bond at the 22, 23-position and is hydrogen or hydroxy;
R$_2$ is alkyl of 1 to 8 carbon atoms, alkenyl of 2 to 8 carbon atoms or cycloalkyl of 3 to 8 carbon atoms;
R$_3$ is hydroxy or methoxy; and the broken line at the 2,3,4-position indicates a double bond at either the 2,3-position or the 3,4-position, which comprises fermenting in a nutrient medium containing sources of carbon, sources of nitrogen and inorganic salts, Saccharopolysporaerythrea ATCC 11635, at a pH of from 5 to 8.5, a temperature of from 20° to 40° C., for from 2 to 10 days, from 0.1 to 10 mg/ml of fermentation medium a compound having the formula:

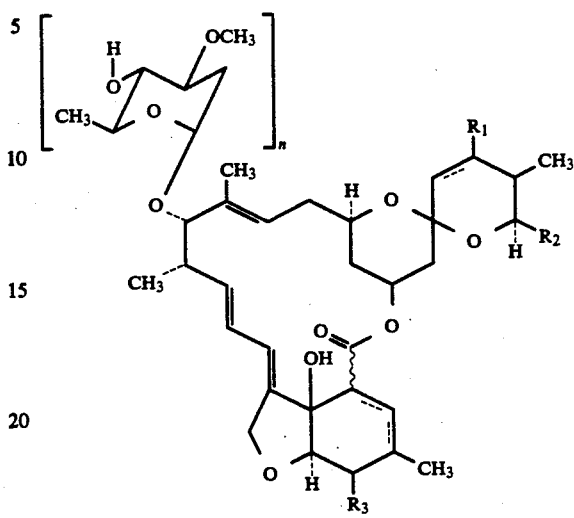

where n, R$_1$, R$_2$, and R$_3$ are as defined above and recovery of the products from the fermentation medium.

2. The process of claim 1 where the broken line at the 22,23-position indicates a 22,23-single bond and R$_1$ is hydrogen;
n is 2;
R$_2$ is isopropyl or sec-butyl;
R$_3$ is hydroxy; and
the broken line at the 2,3,4-position indicates a 3,4-double bond.

3. The process of claim 1 where the starting material is added to the fermentation medium when the fermentation has completed from 10 to 75% of the scheduled term of 2 to 10 days.

4. The process of claim 3 where the starting material is added to the fermentation medium when the fermentation has completed from 20 to 50% of the scheduled term of 2 to 10 days.

5. The process of claim 1 where the starting material is added to the fermentation medium in a quantity of from 1 to 8 mg per ml. of fermentation medium.

* * * * *